(12) United States Patent
Mehrabian

(10) Patent No.: US 9,717,281 B2
(45) Date of Patent: Aug. 1, 2017

(54) UNDERWEAR

(71) Applicant: Hamlet Mehrabian, Burbank, CA (US)

(72) Inventor: Hamlet Mehrabian, Burbank, CA (US)

( * ) Notice: Subject to any disclaimer, the term of this patent is extended or adjusted under 35 U.S.C. 154(b) by 0 days.

(21) Appl. No.: 13/775,060

(22) Filed: Feb. 22, 2013

(65) Prior Publication Data

US 2014/0237704 A1    Aug. 28, 2014

(51) Int. Cl.
  *A41B 9/08*    (2006.01)
  *A41B 9/02*    (2006.01)
  *A61F 13/56*   (2006.01)

(52) U.S. Cl.
  CPC ............. *A41B 9/02* (2013.01); *A41B 9/023* (2013.01); *A61F 13/56* (2013.01)

(58) Field of Classification Search
  CPC ......... A41B 9/001; A41B 9/002; A41B 9/004; A41B 9/005; A41B 9/007; A41B 9/008; A41B 9/02; A41B 9/023; A41B 9/026; A61F 13/64; A61F 13/56; A61F 13/143; A61F 13/148
  USPC ........ 602/62–73, 79; 450/128, 89, 100, 106; 128/98.1; 2/466, 404, 405, 403, 406, 2/400, 401, 402; 604/400, 401, 397, 398
  See application file for complete search history.

(56) References Cited

U.S. PATENT DOCUMENTS

| | | | | |
|---|---|---|---|---|
| 316,903 A | * | 4/1885 | Lytle | 128/98.1 |
| 632,727 A | * | 9/1899 | Kuyath | A61F 13/12 604/308 |
| 655,618 A | * | 8/1900 | Garver | A61F 5/0093 128/98.1 |
| 2,058,970 A | * | 10/1936 | Fiesh | 602/67 |
| 2,310,839 A | * | 2/1943 | Chatfield et al. | 602/67 |
| 2,545,224 A | * | 3/1951 | Butler | A61F 13/64 602/70 |
| 2,599,769 A | * | 6/1952 | MacRae et al. | 2/228 |
| 2,615,445 A | * | 10/1952 | Holmes | 128/98.1 |
| 2,684,673 A | * | 7/1954 | Lerman | A61F 13/00 2/403 |
| 2,713,340 A | * | 7/1955 | Meminger | 128/96.1 |
| 3,247,846 A | * | 4/1966 | Fansler | 602/79 |
| 3,487,833 A | * | 1/1970 | Senser | 602/67 |
| 4,484,919 A | * | 11/1984 | Sohn | A61F 5/4401 604/358 |
| 5,285,531 A | * | 2/1994 | Nalbandian | 2/106 |

(Continued)

*Primary Examiner* — Khoa Huynh
*Assistant Examiner* — Katharine Gracz
(74) *Attorney, Agent, or Firm* — James A. Italia; Italia IP

(57) ABSTRACT

Underwear adapted to add an inner structure to a traditional covering comprising waistband and fabric panels conventionally covering the buttocks, hips, and genital areas. The inner structure may include a fabric panel bearing a ridge intended to occupy the cleft separating the buttocks, with the fabric panel adhering closely to the buttocks. The inner structure may also or instead include a fabric scrotum guard which covers the rear of the scrotum and which separates the scrotum from the inner thighs and separates the right and left perineal folds where inner thighs meet the lowermost trunk. The scrotum guard may include adjustment structure for adjusting tightness of the fit with the Y formed at the scrotum and the entire perineum. The front of the traditional covering may have an opening for retrieving the penis which opening is arranged horizontally rather than in the traditional generally vertical orientation.

9 Claims, 3 Drawing Sheets

(56) References Cited

U.S. PATENT DOCUMENTS 7,122,022 B2 * 10/2006 Drevik .............. A61F 13/47254
  604/385.03
8,672,910 B1 * 3/2014 Kaufman ..................... 604/349

* cited by examiner

UNDERWEAR

FIELD OF THE INVENTION

The present invention relates to foundation garments, and more particularly to underwear having improved accommodation for absorbing sweat and preventing chafing where body tissues would ordinarily abut.

BACKGROUND OF THE INVENTION

Traditional underwear does little other than to cover the buttocks, hips, and genital areas of wearers. In the course of a day, it is possible for body tissues in these areas to rub against one another, thereby producing discomfort due to chafing, or to cause accumulation of perspiration and need for increased hygiene. A need exists in the prior art to overcome these problems.

SUMMARY OF THE INVENTION

The present invention addresses the above stated need by providing underwear which incorporates additional fabric structures adapted to separate body tissues and to absorb accumulation of perspiration and improve hygiene. The novel underwear may include a traditional covering comprising waistband and fabric panels conventionally covering the buttocks, hips, and genital areas. In a first aspect, underwear according to the present invention may comprise an inner structure which may be fixed at the waistband to the traditional covering. This inner structure may comprise a fabric panel bearing a ridge. The fabric is parallel to the outer traditional covering panel, with the ridge, which is generally perpendicular to the fabric panel, arranged to occupy the crack or cleft separating the buttocks. This causes the fabric panel to cover the buttocks in contact therewith. The fabric panel, not being attached to the traditional covering, may then cooperate closely with the buttocks, and will remain in place to intercept and absorb perspiration, and to separate the buttocks to prevent buttock-to-buttock chafing.

In a second aspect, the inner structure may comprise an optional scrotum guard, also of fabric, which covers the rear of the scrotum and which separates the scrotum from the inner thighs and fits in folds of tissue at the perineum. This both prevents chafing and also absorbs any perspiration which may be present and increases hygiene.

The scrotum guard may include adjustment structure for adjusting tightness of the fit with the scrotum and perineal folds.

In a third aspect, the underwear may have an opening for retrieving the penis for urination for example, which opening is arranged horizontally rather than in the traditional generally vertical orientation.

Underwear according to one or more aspects described above may be provided in the form of briefs, or alternatively may have pronounced leg sleeves.

While some of the inner structure is obviously appropriate for male physiology, underwear for females may utilize only the fabric panel bearing the ridge, there being no need for a scrotum guard nor an opening for accessing the penis.

It is an object of the invention to provide underwear which increases comfort by preventing chafing and absorbing perspiration from areas likely to generate perspiration and cause hygiene issues.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
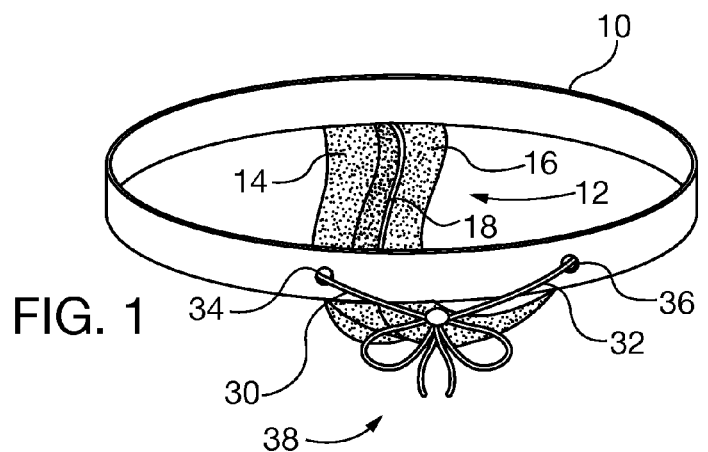
FIG. 1 is a perspective view of an inner component of the underwear of the present invention.

Referring first to FIGS. 1-4, there is shown a waistband 10 and a buttock comfort panel 12 disposed to separate the buttocks and to absorb perspiration from the juncture of the buttocks and keep skin from prolonged touch to skin whereby skin oxygenation or exposure to suitable aeration is compromised. The buttock comfort panel 12 may comprise a single continuous buttock fabric panel formed as two sections or continuous wings 14, two sections or wings 14,16. The wing 14 or 16 projects respectively to the right and to the left of a centrally located ridge 18 which depends from a distal end of the waistband 10 at the rear of the wearer. The ridge 18 is generally perpendicular to the buttock fabric panel formed by the wings 14, wings 14,16, and extends forwardly to a proximal end of the buttocks fabric panel when the underwear associated with the waistband 10 and the buttock comfort panel 12 is worn. It should be mentioned here that the assembly comprising the waistband 10 and the buttock comfort panel 12 may be worn in the manner of an athletic supporter, that is, as a stand alone garment, or alternatively and preferably may be integrated as part of underwear 20 (see FIG. 4) which comprises an outer component in the form of a traditional covering 22 which continuously covers the buttocks, the hips, and the genital region of the wearer. The outer component may be for example conventional underwear (not shown separately) which is devoid of internal constructions of the sort set forth herein. The traditional underwear may comprise a traditional covering waistband and a perineal cover panel disposed to cover the perineus of the wearer. Because the assembly shown in FIG. 1 may be utilized independently of traditional underwear, that assembly may include its own waistband 10, or if integrated with traditional underwear, the assembly shown in FIG. 1 may utilize the waistband of the traditional underwear.

Figure 7:
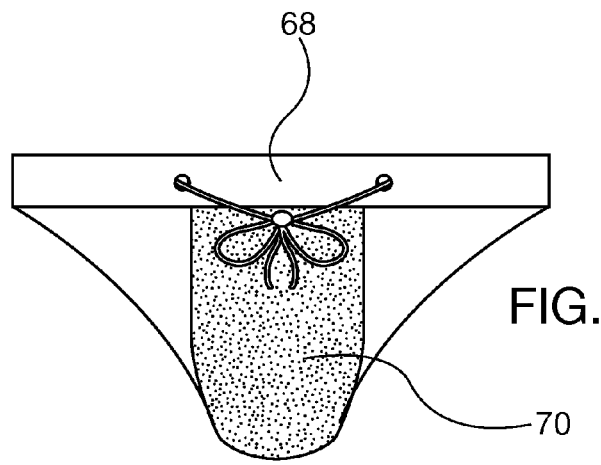
FIG. 7 is a front view of underwear according to still another aspect of the invention.
Figure 8:
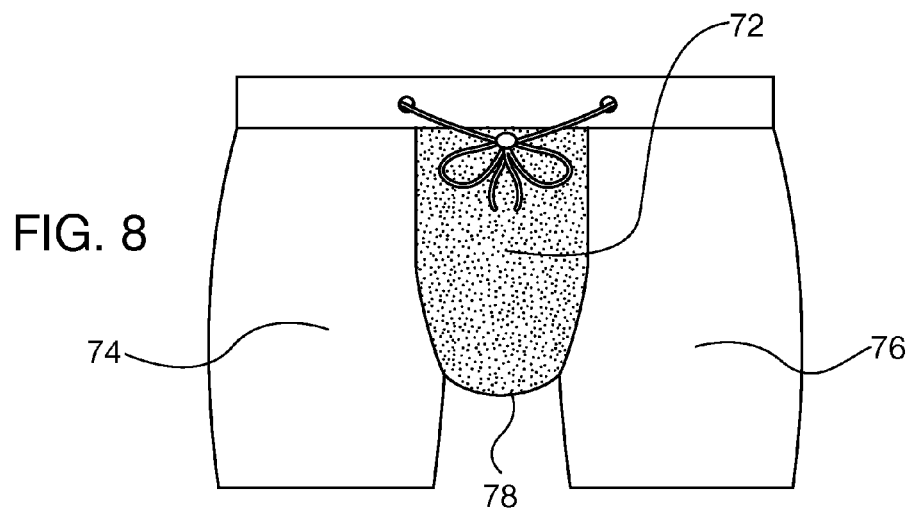
FIG. 8 is a front view of underwear according to a further aspect of the invention.

The buttock comfort panel 12 is coupled to or anchored at the waistband 10 at the rear of the underwear, and terminates in a terminus at the scrotum of male wearers. The terminus is used as a term of convenience, and merely designates the forwardmost end of the ridge 18. The buttock comfort panel 12 may be utilized in underwear for female wearers (as shown in FIGS. 7 and 8). In either case, the buttock comfort panel 12 comprises an anchoring member, the side ridges of which fit into the folds of the right and left perineal croaches, which is ultimately attached to the waistband 10 at the front of the wearer. For use by females, the ridge resembling a "Y" still exists where the fabric structure is not split for scrotum accommodation as in the case of a male wearer.

When provided as part of underwear intended for use by females, the anchoring member may comprise a fabric panel devoid of structural features more complicated than an expanse of planar fabric, such as the fabric panel 22.

Figure 2:
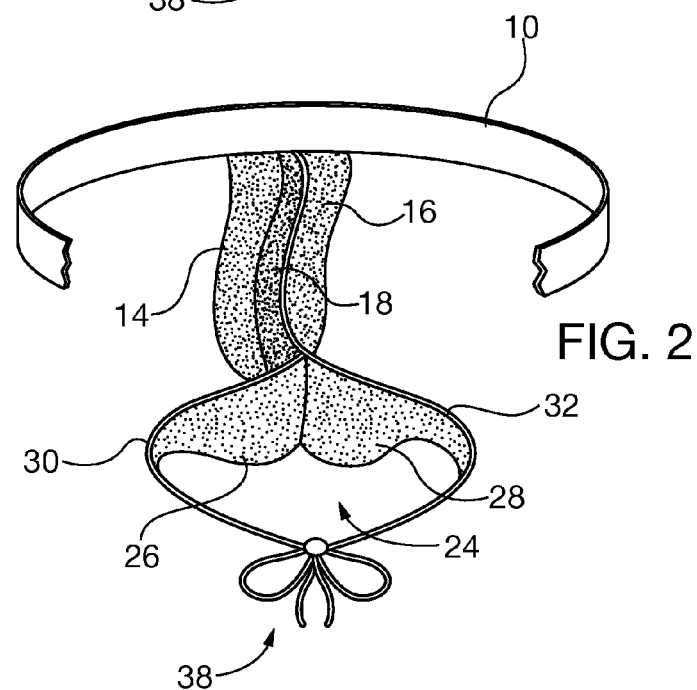
FIG. 2 is similar to FIG. 1, but is broken away to better show internal detail.
Figure 3:
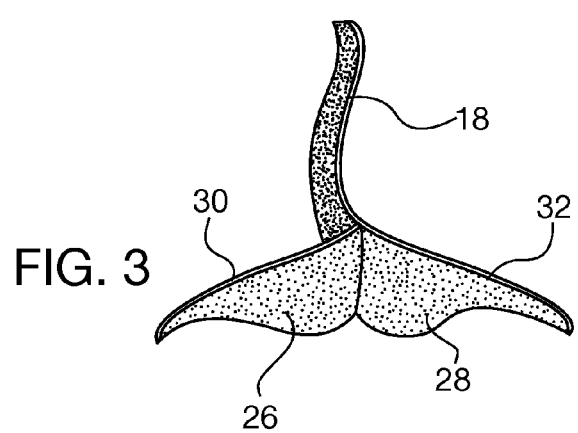
FIG. 3 is a perspective detail view of internal detail revealed to view in FIG. 2.

Referring specifically to FIG. 2, when provided as part of underwear intended for use by males, the anchoring member may comprise a scrotum guard 24 located at the terminus of the buttock comfort panel 12. The scrotum guard 24 may comprise two sections including a right side continuation 26 of the ridge 18 of the buttock comfort panel 12 and a left side continuation 28 of the ridge 18 of the buttock comfort panel 12. The right side continuation 26 and the left side continuation 28 are clearly visible in FIG. 2, and for further clarity of view are shown to a greater degree of isolation from other components of the underwear in FIG. 3. When viewed in plan, right side continuation 26, the left side continuation 28, and the buttock comfort panel 12 form a Y. The right side continuation 26 and the left side continuation 28 each project forwardly of the buttock comfort panel 12 and contact and connect to the waistband 10 at its front.

It should be mentioned here that orientational terms such as forward, forwardly, right, left, front, and rear refer to the subject drawing as viewed by an observer. The drawing figures depict their subject matter in orientations of normal use, which could obviously change with changes in body posture and position. It will be assumed for convenience that the underwear is worn by a person standing upright, such that the waistband 10 occupies a horizontal plane for example. Therefore, orientational terms must be understood to provide semantic basis for purposes of description, and do not limit the invention or its component parts in any particular way.

Also, it is appreciated that the novel underwear will be fabricated mostly if not exclusively from relatively flaccid natural and some synthetic fabrics, or combinations thereof. Therefore, description of direction of projection of the component members of the underwear refers to the underwear as depicted in the various drawing figures, it being understood that due to flexibility and flaccidity of the constituent materials, the underwear will inevitably deform in the course of use and not literally conform to the geometric relationships set forth herein.

Contact and connection of the right side continuation 26 and the left side continuation 28 to the waistband 10 is accomplished by drawstrings 30, 32. The drawstrings 30, 32 are intended to be passed through respective holes 34, 36 formed in the waistband 10, as seen in FIG. 1, and may be tied in a knot 38. The drawstrings 30, 32 provide an adjustment feature disposed to fix the scrotum guard 24 selectively at plural distances from the front of the underwear. Pulling on the drawstrings 30, 32 such that progressively more of the drawstrings 30, 32 has passed forwardly of the waistband 10 will cause the scrotum guard 24 to advance towards the front of the underwear and at the same time adjust the tightness of the entire ridge inside perineal clefts. Where corresponding underwear is produced for use by females, the scrotum guard 24 may be omitted, with suitable modifications introduced there instead. The user may adjust the scrotum guard 24 to suit his own comfort. When the drawstrings 30, 32 are tied in the knot 38, the drawstring arrangement engages the waistband 10, thereby anchoring the combined buttock comfort panel 12 and scrotum guard 24 to the front of the waistband 10. It should be mentioned here that for clarity of the view, the drawstrings 30, 32 are not depicted as having been drawn tight, as would occur in actual use. The combined buttock comfort panel 12 and scrotum guard 24 are therefore supported at the front of the underwear by the drawstrings 30, 32 and at the rear of the underwear by attachment to the waistband 10.

Figure 4:
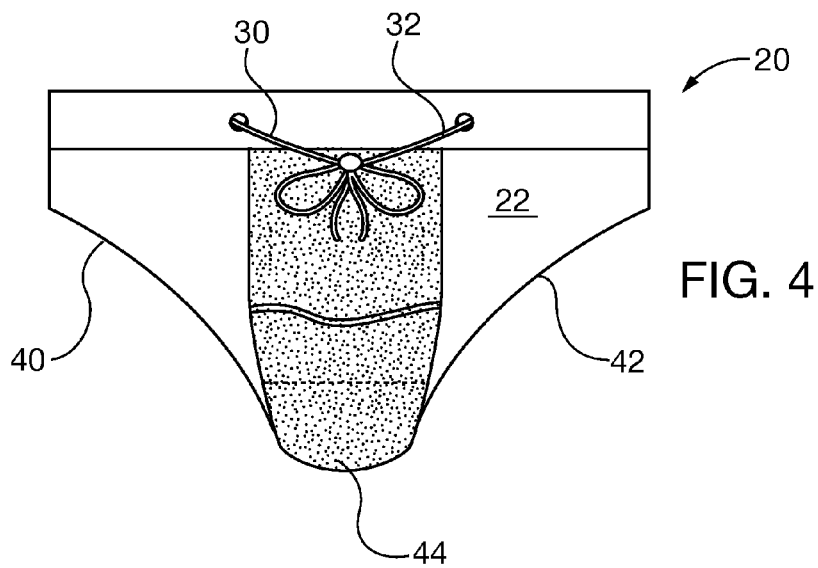
FIG. 4 is a front view of underwear according to at least one aspect of the invention.

FIG. 4 shows a form of underwear according to the present invention wherein the assembly of FIG. 1 has been integrated with underwear 20 wherein the traditional covering 22 includes leg openings 40, 42 which are located above the perineal cover panel 44 of the traditional covering 22.

Figure 5:
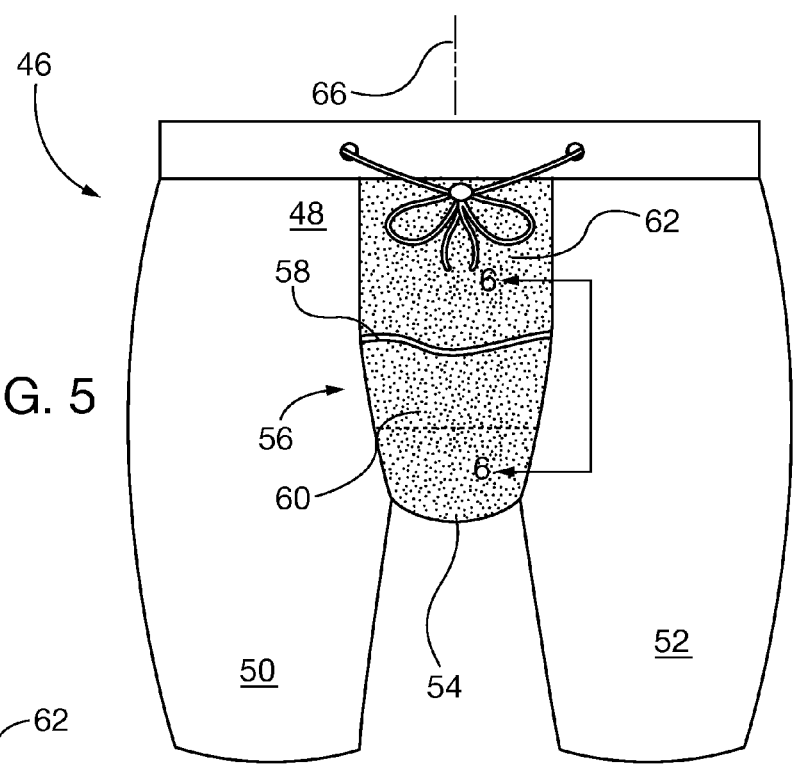
FIG. 5 is a front view of underwear according to at least one further aspect of the invention.

FIG. 5 shows a form of underwear wherein the assembly of FIG. 1 has been integrated with underwear 46, wherein the traditional covering 48 includes leg sleeves 50, 52 which project below the perineal cover panel 54. The leg sleeves 50, 52 may be dimensioned and configured to cling to the leg of the wearer when the underwear is worn. This is typical of underwear such as boxer briefs, and typically includes elastic characteristics in the constituent fabric. Alternatively, the leg sleeves 50, 52 may be dimensioned and configured to be relatively greater in diameter than the width of the wearer's leg when the underwear is worn, as is typical of so-called boxer type shorts.

Figure 6:
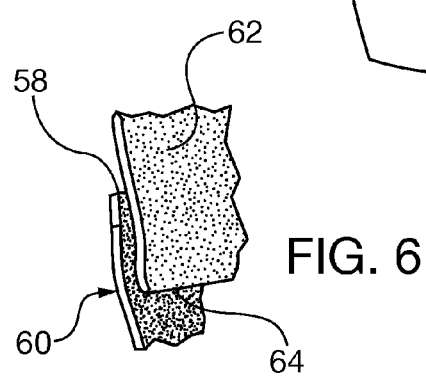
FIG. 6 is a side detail view taken along line 6-6 in FIG. 5.

FIGS. 5 and 6 show a further feature of the invention, namely, a fly 56 having opening length in a horizontal direction. The opening length may coincide with the direction of a horizontally extending upper edge 58 of a lower panel 60. The fly 56 may comprise an upper panel 62 which extends from above the upper edge 58 of the lower panel 60 to below the upper edge 58 of the lower panel 60. The lower edge 64 of the upper panel 62 is well below the upper edge of the lower panel 60. That portion of the upper panel 62 which lies below the upper edge 58 may be considered a lower extremity of the upper panel 62. This lower extremity is located inside the lower panel 60. That is, the lower extremity is located at a smaller radius from the vertical centerline 66 of the underwear than the lower panel 62.

Turning now to FIG. 7, the underwear depicted therein is suitable for use by female wearers. To that end, that member which is ultimately attached to the waistband 68 at the front of the wearer comprises a fabric panel 70 which is devoid of a fly such as the fly 56 of FIG. 5.

FIG. 8 shows underwear having a similar fabric panel 72, but with leg sleeves 74, 76 of length such that they terminate below the perineal cover 78 of the underwear.

Figure 9:
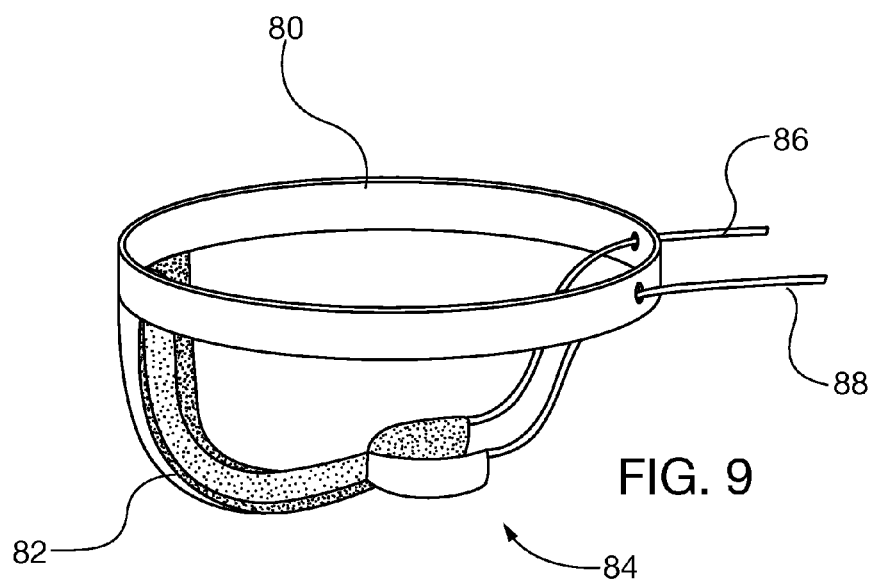
FIG. 9 is a side perspective view of underwear according to still another aspect of the invention.

The various features of the present invention may be provided in any combination which is feasible. Illustratively, and referring to FIG. 9, there is shown underwear comprising a waistband 80, a rear buttocks panel 82 which is devoid of structure such as the buttock comfort panel 12, being generally planar (if laid on a planar surface), and a scrotum guard 84. The scrotum guard 84 may be the structural and functional equivalent of the scrotum guard 24 for example. This option allows users to omit the buttock comfort panel 12 while still enjoying the benefits of the scrotum guard 84 and, or separation of perineal folds at right and left sides of the crotch or clefts. The rear buttocks panel 82 depends from the waistband 80 at the rear of the underwear. The scrotum guard 84 may be adjusted and supported by drawstrings 86, 88 in the manner of the underwear of FIG. 1. It should be noted that for use by females, the scrotum guard 84 may be omitted or suitably modified.

The present invention is susceptible to modifications and variations which may be introduced thereto without departing from the inventive concept. Illustratively, the arrangement of drawstrings 30 and 32 may be replaced by an arrangement (not shown) using snaps or other fasteners, or by an arrangement using elastic straps anchored to the waistband such as the waistband 10. The arrangement of elastic straps could utilize hook and loop material, buttons, or engagement of eyelets formed either in the straps or in the waistband.

In another variation, a protective pad or liner located at the anus area may be incorporated into the novel underwear. Such a disposable pad may have an associated fastening element such as adhesive or may be sufficiently nappy as to adhere naturally to the constituent material of the underwear. Although the pad or liner may be fabric, it may also be entirely or partially a paper material for example. The pad or liner may be removable and washable, or alternatively, may be disposable. Preferably, the pad or liner may comprise a soft, fleece-like material yet may be thin enough so as not to cause discomfort.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. Underwear to be worn by a wearer comprising:
a waistband having a front and rear portion, the front portion including holes;
a single continuous buttock fabric panel comprised of first and second continuous wing structures that depends from a distal end of the rear portion of the waistband and extends to a proximal end of the buttocks fabric panel, wherein the first and second continuous wings further comprise a ridge located between said wings, wherein the ridge is a single continuous ridge that extends from a top of the distal end towards a terminus at the proximal end and which is formed by said wings, such that the ridge is generally perpendicular to the buttock fabric panel, wherein the ridge extends forwardly when the underwear is worn, such that the ridge occupies the crack or cleft separating the buttocks and thereby remains in place to intercept and absorb perspiration, and to separate the buttocks to prevent buttock-to-buttock chafing;
a scrotum guard located at the terminus of the ridge, comprising a right side continuation of the ridge and a left side continuation of the ridge, wherein the right side continuation, the left side continuation, and the ridge form a Y when viewed in plan, and wherein the right side continuation and the left side continuation are adapted to fit in folds of tissue at a perineum and cooperate to cover rear and sides of a scrotum thereby separating the scrotum for inner thighs, wherein each continuation terminates in an anchoring member which attached to the front portion of the waistband each project forwardly of the ridge and contact and connect to the front portion of the waistband and;
an adjustment feature disposed to fix the scrotum guard selectively at plural distances from a front of the underwear; wherein the adjustment feature comprises a drawstring arrangement which is coupled to the scrotum guard and which loops through the holes in the waistband at the front of the underwear.

2. The underwear of claim 1, further comprising a fly having opening length in a horizontal direction.

3. The underwear of claim 2, wherein the fly comprises a lower panel having a horizontally extending upper edge and an upper panel which extends from above the horizontally extending upper edge of the lower panel to below the horizontally extending upper edge of the lower panel and which said upper panel includes a lower extremity located inside the lower panel.

4. The underwear of claim 1, further comprising a traditional covering which continuously covers the buttocks, the hips, and the genital region, and which comprises a perineal cover panel disposed to cover the perineum, and which is connected at the rear portion of the waistband.

5. The underwear of claim 4, wherein the traditional covering includes leg openings which are located above the perineal cover panel.

6. The underwear of claim 4, wherein the traditional covering includes leg sleeves which project below the perineal cover panel.

7. The underwear of claim 6, wherein the leg sleeves are dimensioned and configured to cling to a leg of the wearer when the underwear is worn.

8. The underwear of claim 6, wherein the leg sleeves are dimensioned and configured to be relatively greater in diameter than a length of the wearer when the underwear is worn.

9. Underwear to be worn by a wearer comprising:
a waistband having a front and rear portion, the front portion including holes;
a single continuous rear buttocks panel comprised of first and second continuous wing structures that depends from a distal end of the waistband at a rear of the underwear and extends to a proximal end of the rear buttock panel, wherein the first and second continuous wings further comprise a ridge located between said wings wherein the ridge is a single continuous ridge that extends from a top of the distal end towards a terminus at the proximal end; and,
a scrotum guard coupled to the proximal end of the rear buttocks panel, comprising a right side continuation of the rear buttocks panel and a left side continuation of the rear buttocks panel, wherein the right side continuation, the left side continuation, and the rear buttocks panel form a Y when viewed in plan, and wherein the right side continuation and the left side continuation fit in folds of tissue at a perineum and cooperate to cover rear and sides of the scrotum thereby separating the scrotum from inner thighs, such that the scrotum guard remains in place to intercept and absorb perspiration and prevent scrotum-to-thigh chafing, and wherein the right side continuation and left side continuations project forwardly of the rear buttocks panel and contact and connect to the waistband at a front of the underwear; and
an adjustment feature disposed to fix the scrotum guard selectively at plural distances from a front of the underwear; wherein the adjustment feature comprises a drawstring arrangement which is coupled to the scrotum guard and which loops through the holes in the waistband at the front of the underwear.

\* \* \* \* \*